United States Patent [19]

Baumann

[11] 4,192,997
[45] Mar. 11, 1980

[54] TOMOGRAPH FOR PRODUCING TRANSVERSE LAYER IMAGES

[75] Inventor: Heinz Baumann, Buckenhof, Fed. Rep. of Germany

[73] Assignee: Siemens Aktiengesellschaft, Berlin & Munich, Fed. Rep. of Germany

[21] Appl. No.: 948,427

[22] Filed: Oct. 4, 1978

[30] Foreign Application Priority Data

Nov. 11, 1977 [DE] Fed. Rep. of Germany ....... 2750633

[51] Int. Cl.² .................... A61B 6/00; H05G 1/08; H05G 1/20
[52] U.S. Cl. .................................. 250/445 T; 250/421
[58] Field of Search ................... 250/445 T, 421, 422, 250/419

[56] References Cited

U.S. PATENT DOCUMENTS

| 2,365,855 | 12/1944 | Atlee | 250/421 |
| 2,659,015 | 11/1953 | Lee | 250/421 |
| 4,093,859 | 6/1978 | Davis et al. | 250/445 T |

*Primary Examiner*—Alfred E. Smith
*Assistant Examiner*—T. N. Grigsby
*Attorney, Agent, or Firm*—Hill, Van Santen, Steadman, Chiara & Simpson

[57] ABSTRACT

In an illustrative embodiment, a medium frequency generator is utilized, and at least the components on the high-voltage side of the X-ray generator and the medium frequency generator are mounted on the rotating frame, and a stationary energy supply installation, for example, a mains rectifier, for the purpose of energy transmission.

5 Claims, 6 Drawing Figures

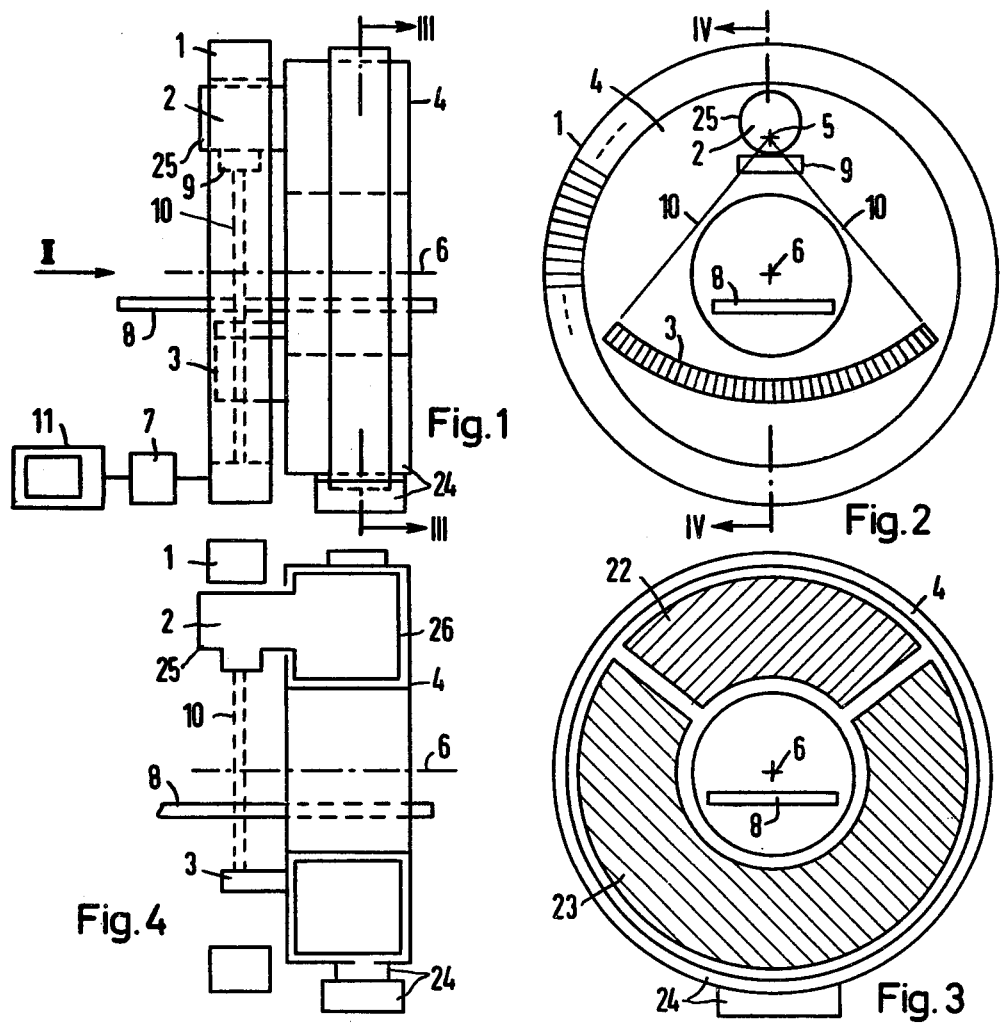
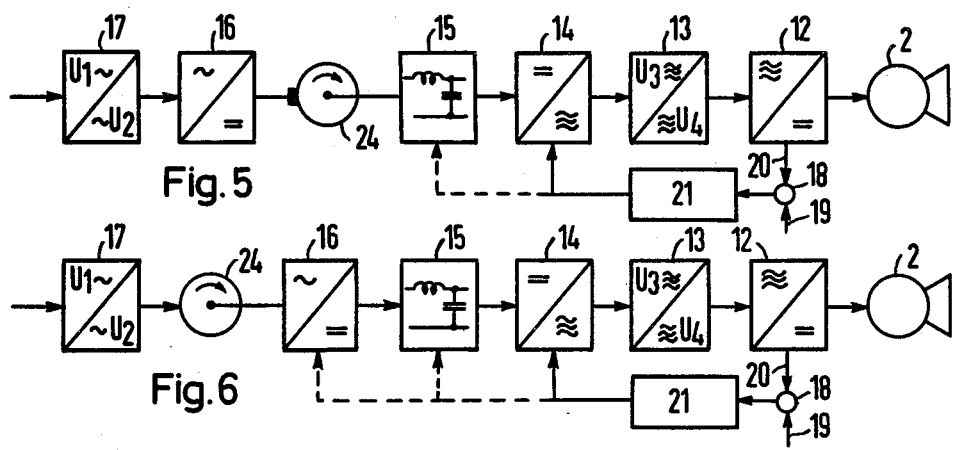

TOMOGRAPH FOR PRODUCING TRANSVERSE LAYER IMAGES

BACKGROUND OF THE INVENTION

The invention relates to a tomographic apparatus for producing transverse layer images of an exposure subject, with a radiation measuring arrangement with an X-ray source supplied by an X-ray generator which produces an X-ray beam penetrating the exposure subject, of which the cross-sectional extent perpendicular to the layer plane is equal to the layer thickness, with a radiation receiver which determines the radiation intensity behind the subject by scanning the projected X-ray beam, with a rotating frame for rotating the X-ray source in the layer plane to scan the exposure subject in different directions, and with a measured value converter to transform the signals supplied by the radiation receiver into a layer image.

Efforts are being made to keep the image exposure time in a tomograph of this type as short as possible. The image exposure time is essentially determined by the duration of an exposure cycle, i.e., by the mechanical structure of the apparatus. A tomograph of the type specified at the outset is described, for instance, in German Offenlegungsschrift No. 24 37 710. In this known tomograph, the X-ray generator is disposed stationarily and is connected to the X-ray tube by high voltage cables. These cables must form a loop, so the the X-ray tube is mobile for scanning the exposure subject, and such cables are heavy so as to increase the mass which must be moved with the X-ray tube during an exposure.

SUMMARY OF THE INVENTION

The object underlying the invention is to develop a tomograph of the type specified at the outset with regard to its construction such as to render possible rapid movement of the X-ray source for scanning an exposure subject and thus a short image build-up time.

According to the invention, this object is achieved by the fact that the high voltage transformer is operated with a frequency which is higher than the mains frequency (i.e. with a medium frequency), that at least the structural elements of the X-ray generator on the high voltage side along with the medium frequency generator are fixed to the rotating frame and that a rotating current coupling is provided for the transfer of energy between the rotating frame and a stationary energy supply apparatus. There is no need in the tomograph according to the invention to run high voltage cables to the X-ray source. Coupling between the generator parts, disposed on the rotating frame, and the energy supply apparatus may be made, by way of example, via a brush-slip ring arrangement. When the X-ray source is moved, therefore, there are no heavy cables to be moved with it, so that very short image build-up times are possible.

Constructing the X-ray generator as a medium frequency generator with a mains rectifier and an inverter supplying the high voltage transformer enables the high voltage transformer of the X-ray generator to be small and light weight in construction, so that there are no large volumes to be accelerated and braked in order to scan an exposure subject. In a particularly expedient development of the invention, designing the radiation receiver as a stationary detector ring is suggested, the X-ray source being mounted within the detector ring for rotation about the central axis of the detector ring. In this arrangement, the radiation receiver is not moved when an exposure subject is being scanned, so that the lines running to it can be disposed stationarily.

The invention is explained in detail below with reference to two embodiments represented in the drawings; and other objects, features and advantages will be apparent from this detailed disclosure.

BRIEF DESCRIPTION OF THE DRAWINGS

FIG. 1 shows a lateral view of a tomographic apparatus in accordance with the invention;

FIG. 2 shows a view of the tomograph in accordance with FIG. 1 taken in the direction of the arrow II;

FIG. 3 shows a section along line III—III in FIG. 1;

FIG. 4 shows a section along line IV—IV in FIG. 2; and

FIGS. 5 and 6 show circuit diagrams to explain FIGS. 1 to 4.

DETAILED DESCRIPTION

The tomograph represented in FIGS. 1 to 4 has a circularly designed radiation receiver 1 consisting of a series of detector elements. It encloses an X-ray tube 2 and a collimator 3, these being attached to a rotating frame 4. With the X-ray tube 2 and collimator 3 whose laminae are aligned with the focus 5 of the X-ray tube 2, the rotating frame 4 is rotatable about the axis 6 of the radiation receiver 1. The radiation receiver 1 is connected to a measured value converter 7 which from the output signals of the detector elements of the radiation receiver 1 produced while the X-ray tube 2 rotates through an angle of 360°, calculates the absorption values of present points of a transverse layer of a patient lying on a couch 8. To form the X-ray beam penetrating the patient, a collimator 9 is attached to the X-ray tube 2 which collimates a fan-shaped beam 10 of X-ray whose spread is selected such that it penetrates the entire transverse layer for investigation of a patient lying on the couch 8 and that its dimension perpendicular to this layer is equal to the layer thickness. The absorption values calculated by the measured value converter 7 are reproduced on a video device 11 as a transverse layer image in the form of grey values. For the sake of simplicity, the measured value converter 7 and the video device 11 are only represented in FIG. 1.

From the circuit diagram according to FIG. 5 it is clear that the X-ray tube 2 is connected to a high voltage rectifier 12 which is supplied by a high voltage transformer 13. The primary energy is conveyed to the high voltage transformer 13 by an inverter 14 which is supplied via a direct voltage intermediate circuit 15 containing an LC element by a mains rectifier 16. Connected before the mains rectifier 16 is a further mains adjusting member 17. The frequency of the inverter 14 is a medium frequency in the kHz range. The high voltage transformer 13 may therefore be made light weight and small in construction. A desired value signal for the X-ray tube voltage is supplied to a comparator 18 at an input 19 and an actual value signal for this voltage is supplied at the input 20. Via a kV control device 21 any resultant difference signal from comparator 18 influences the inverter 14 or the direct current intermediate circuit 15 for the purpose of keeping the X-ray tube voltage constant.

The structural elements 2 and 12, 13, 14, 15, 18, 21 are attached to the rotating frame 4, as explained hereafter in reference to FIG. 3. The high voltage transformer 13 with the high voltage rectifier 12 is here disposed in the space 22, whilst the structural elements 14, 15, 18, 21 are located in the space 23. Energy is supplied to the direct voltage intermediate circuit 15 via a brush slip ring arrangement 24 FIGS. 3 and 4. The structural elements 2, 12, 13, 14, 15, 18, 21 thus rotate at the same time as the rotating frame 4 rotates. There are no heavy cables at all to be moved during this rotation, so that the rotation can be made very rapidly. The design of the X-ray generator according to FIG. 5 as a medium frequency generator produces a particularly light-weight and space-saving construction which renders a very short scanning time possible. The direct current intermediate circuit 15 acts as low pass filter for mains interferences and for interferences caused by the slip ring transfer. This interference does not therefore have an adverse effect on the X-ray tube voltage. The lines in the medium frequency circuit can be kept very short so that their inductance poses no problems. The pure control signals, e.g. for switching the radiation on and off, may be transferred contactlessly, e.g. via light or ultrasonic radiation. The X-ray tube 2 is housed according to FIGS. 1, 2, 4 in a housing 25 projecting axially on the rotating frame 4, said housing forming together with a housing 26 (FIG. 4), in which the structural elements 12, 13 are located, an oil-filled tank.

Disposing several X-ray tubes, instead of one single X-ray tube 2, on the rotating frame 4, and offset angularly from one another, is conceivable within the scope of the invention. In this case, there is the further reduction of the scanning time relative to the instance represented where a single X-ray tube is used, since the angle of rotation can be smaller than in the embodiment represented.

The structural elements of the high voltage generator can also be arranged according to FIG. 6. Here the structural elements are identical with the structural elements according to FIG. 5. The difference of the embodiment according to FIG. 5 is that the brush slip ring arrangement 24 is disposed between the mains adjusting member 17 and the mains rectifier 16, thus that the mains rectifier 16 lies on the rotating frame 4 in the example according to FIG. 6. Whilst in the example according to FIG. 5 direct current is transferred by the brush slip ring arrangement 24, in FIG. 6 the brush slip ring arrangement 24 transfers alternating current. The X-ray tube voltage can also be regulated in the example according to FIG. 6 via the rectifier 16. The rectifier 16 can also be disposed in the space 23. The structural parts in the spaces 22, 23 are not represented in FIG. 3 for the sake of simplicity.

It will be apparent that many modifications and variations may be effected without departing from the scope of the novel teachings and concepts of the present invention.

I claim as my invention:

1. Tomographic apparatus for producing transverse layer images of an exposure subject, with an X-ray source, and X-ray generator including a high voltage transformer supplying the X-ray source to produce an X-ray beam penetrating the exposure subject, of which the cross-sectional extent perpendicular to the layer plane is the same as the layer thickness, with a radiation receiver which determines the radiation intensity behind the subject by scanning the projected X-ray beam, with a rotating frame for rotating the X-ray source in the layer plane to scan the exposure subject in different directions and with a measured value converter to transform the signals supplied by the radiation receiver into a layer image, characterized in that a medium frequency generator (14) supplies the high voltage transformer with a medium frequency which is higher than the mains frequency, that at least the structural elements on the high voltage side (12, 13, 18, 21) of the X-ray generator (12 to 21) are fixed along with the medium frequency generator (14) on the rotating frame (4) and that a rotating current coupling (24) is provided to transfer the energy between the rotating frame (4) and a stationary energy supply apparatus (16, 17, FIG. 5; or 17, FIG. 6).

2. Tomographic apparatus according to claim 1, characterized in that the current coupling is formed by a brush-slip ring arrangement (24).

3. Tomographic apparatus according to claim 1, characterized in that the X-ray generator (12 to 21) has a mains rectifier (16) and an inverter (14) supplying the high voltage transformer (13), and that the mains rectifier (16) is stationary and is coupled via the rotating current coupling (24) with the medium frequency generator (14) fixed on the rotating frame (14).

4. Tomographic apparatus according to claim 1, characterized in that the X-ray generator (12 to 21) has a mains rectifier (16) supplying the medium frequency generator (14) and that all the structural elements (14, 15, 16, 18) connected before the primary winding of the high voltage transformer (13) including the mains rectifier (16) are fixed on the rotating frame (4).

5. Tomographic apparatus according to claim 1, characterized in that the X-ray source (2) is housed in a housing (25) projecting axially on the rotating frame (4), said housing forming with a housing (26) disposed in the rotating frame (4) a tank for accommodating structural elements (12, 13) of the X-ray generator (12-21).

* * * * *